US010883972B2

(12) United States Patent
Tabassum et al.

(10) Patent No.: US 10,883,972 B2
(45) Date of Patent: Jan. 5, 2021

(54) COATING TESTER USING GAS SENSORS (71) Applicant: Applied Materials, Inc., Santa Clara, CA (US)

(72) Inventors: Tasnuva Tabassum, Waldorf, MD (US); Mats Larsson, Sunnyvale, CA (US); Kevin A. Papke, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 299 days.

(21) Appl. No.: 15/429,038

(22) Filed: Feb. 9, 2017

(65) Prior Publication Data
US 2018/0224412 A1 Aug. 9, 2018

(51) Int. Cl.
*G01N 33/00* (2006.01)
*G01N 33/2025* (2019.01)

(52) U.S. Cl.
CPC ....... *G01N 33/005* (2013.01); *G01N 33/2025* (2019.01); *G01N 2033/0095* (2013.01); *G01N 2033/0096* (2013.01)

(58) Field of Classification Search
USPC ............................................................ 436/5
See application file for complete search history.

(56) References Cited

U.S. PATENT DOCUMENTS

| 4,473,795 A | 9/1984 | Wood |
| 5,373,734 A | 12/1994 | Shih et al. |
| 8,854,451 B2 | 10/2014 | Cormier et al. |
| 2011/0315550 A1 | 12/2011 | Zhang et al. |
| 2015/0301010 A1 | 10/2015 | Valentini |

FOREIGN PATENT DOCUMENTS

JP  63-238460  10/1988

OTHER PUBLICATIONS

Sparkfun Electronics, Hydrogen Gas Sensor, 2013. Retrieved from internet https://web.archive.org/web/20130131061624/https://www.sparkfun.com/products/10916.*
Detcon Inc., Model DM-702-H2 detcon inc. Hydrogen Sensor (1%), 2011, retrieved from internet site: https://web.archive.org/web/20110523200041/http://www.detcon.com/1-documents/data_sheets/1-sensors/Model%20700/DM-700/Hydrogen%20DM-702-H2%201%20Percent.pdf.*
PCT Notification of Transmittal of the International Search Report and the Written Opinion of the International Searching Authority for International Application No. PCT/US2018/014269; dated May 4, 2018; 13 total pages.

* cited by examiner

*Primary Examiner* — Xiaoyun R Xu
(74) *Attorney, Agent, or Firm* — Patterson + Sheridan, LLP (57) ABSTRACT

Embodiments of the disclosure generally relate to a system, apparatus and method for testing a coating over a semiconductor chamber component. In one embodiment, a test station comprises a hollow tube, a sensor coupled to a top end of the tube and a processing system communicatively coupled to the sensor. The hollow tube has an open bottom end configured for sealingly engaging a coating layer of the semiconductor chamber component. The sensor is configured to detect the presence of a gaseous byproduct of a reaction between a reagent disposed in the hollow tube and a base layer disposed under the coating layer. The processing system is configured to determine exposure of the base layer through the coating layer in response to information about the presence of the gaseous byproduct. In another embodiment, the processing system is communicatively coupled to each sensor of a plurality of test stations.

16 Claims, 5 Drawing Sheets

COATING TESTER USING GAS SENSORS

BACKGROUND

Field

Embodiments of the disclosure generally relate to a system, apparatus and method for testing a coating disposed over a semiconductor chamber component.

Description of the Related Art

In the field of semiconductor material processing, apparatuses like vacuum processing chambers are used for etching and deposition of various materials on substrates. The processing chambers include semiconductor chamber components, many of which are fabricated from metal alloys.

Semiconductor chamber components fabricated from coated metal alloys provide unique properties such as high corrosion resistance, high surface micro-hardness, high plasma resistance, and low cost of ownership compared to semiconductor chamber components comprised of bare metal. However, when the coating layer fails, etchants, often halides, react with the underlying metal exposed below the coating layer. Thus, poor coating leads to a short service life, severe corrosion, high particles, and high contamination of the processed substrates.

Thus, there is a need for a system, apparatus and method for testing a coating disposed over a semiconductor chamber component.

SUMMARY

Embodiments of the disclosure generally relate to a system, apparatus and method for testing a coating disposed over a semiconductor chamber component. In one embodiment, a test station for testing a coating includes a hollow tube, a sensor coupled to a top end of the tube and a processing system communicatively coupled to the sensor. The hollow tube has an open bottom end configured for sealingly engaging a coating layer of the semiconductor chamber component. The sensor is configured to detect the presence of a gaseous byproduct of a reaction between a reagent disposed in the hollow tube and a base layer of the semiconductor chamber component disposed under the coating layer. The processing system is configured to determine exposure of the base layer through the coating layer in response to information about the presence of the gaseous byproduct obtained by the sensor.

In another embodiment of the disclosure, a system for testing a coating over a semiconductor chamber component is provided. The system includes a plurality of test stations and a processing system communicatively coupled to each of the plurality of test stations. Each test station includes a hollow tube and a sensor coupled to a top end of the tube. The hollow tube has an open bottom end configured for sealingly engaging a coating layer of the semiconductor chamber component. The sensor is configured to detect the presence of a gaseous byproduct of a reaction between a reagent disposed in the hollow tube and a base layer of the semiconductor chamber component disposed under the coating layer. The processing system is communicatively coupled to each sensor and configured to determine exposure of the base layer through the coating layer in response to information about the presence of the gaseous byproduct obtained by each sensor.

Yet another embodiment provides a method for testing a coating disposed over a semiconductor chamber component. The method includes exposing a coating layer of a first semiconductor chamber component to a reagent that is inert to the coating layer and reactive with a base layer of the first semiconductor chamber component disposed under the coating layer and detecting by a first sensor a presence of a gaseous byproduct of a reaction between the reagent and the base layer.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that the elements and features of one embodiment may be beneficially incorporated in other embodiments without further recitation.

DETAILED DESCRIPTION

Embodiments of the disclosure generally relate to a system, apparatus and method for testing a coating disposed over a semiconductor chamber component.

Components of a semiconductor processing chamber are often made of coated metal parts of aluminum or steel. In order to evaluate the presence of defects in the coating layer, a test is implemented using reagents that are reactive with a base metal layer of the semiconductor chamber component, but substantially inert to the coating layer. The reagents are often acids. The testing is often destructive, and can be utilized for quality control and production testing for lots of semiconductor chamber components during manufacturing. The productivity, defect and particle performance as well as metal contamination during plasma processes rely on the quality of the coatings. Coatings having high corrosion resistance can provide much better productivity performance for plasma etch and deposition tools. On the other hand, defective coatings on the components can lead to a short service life, severe corrosion, and high cost of ownership of the component and processing system itself, along with high particles counts, processing defects, and high metal contamination of plasma-processed substrates. Therefore, testing is an important aspect for coatings on metal parts in chamber components in the semiconductor industry. Coatings can be optimized to meet demand specifications from customers in order to survive a certain number of cycles within the chamber before corroding or failing.

The present disclosure shows an apparatus, which may be automated, and an efficient method which offers a quantitative measure of failures of coating layers as well as a qualitative verification that defects are indeed present in the coating layer. A gas sensor connected to the apparatus and capable of detecting the effusion of a gaseous byproduct during the testing is used. The presence of defects in the coating layer allows a reagent to penetrate through the coating layer and react with the underlying base layer material, thus releasing the gaseous byproduct. The sensor detects the presence of the gaseous byproduct, for example, in the form of an increase in the voltage or current across simple circuitry connected to the sensor. The increase in voltage or current is monitored through a processing system. The apparatus is configured as a test station, as described in FIG. 1.

Figure 1:
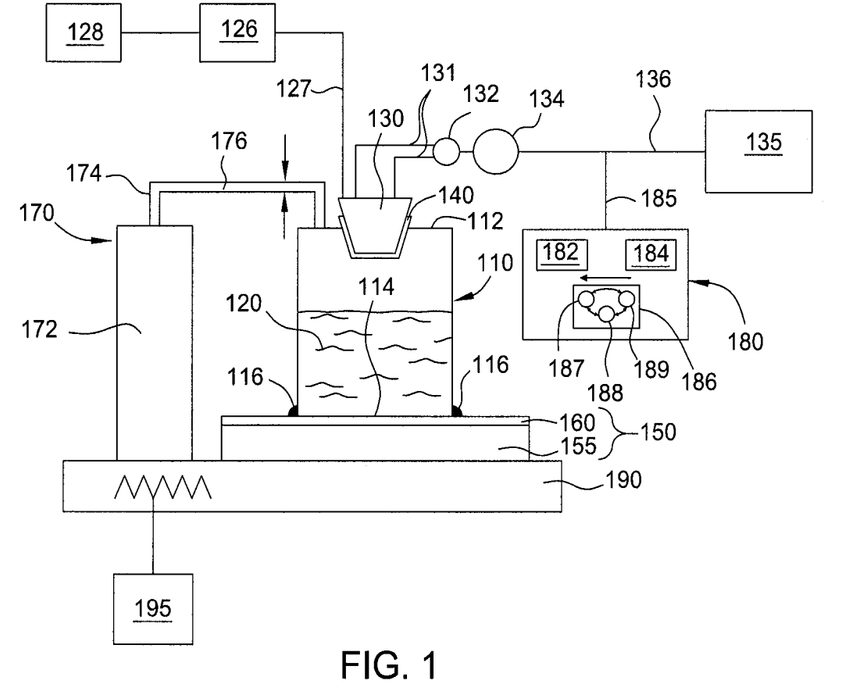
FIG. 1 is a schematic representation of a test station for testing a non-defective coating over a semiconductor chamber component.
Figure 2:
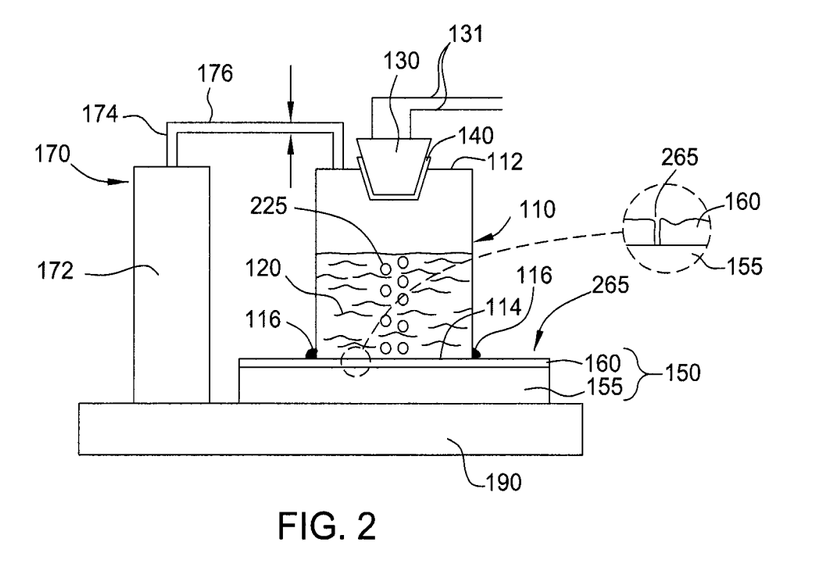
FIG. 2 is a schematic view of a test station for testing a defective coating over the semiconductor chamber component.

Referring to FIG. 1, a coupon 150, which may be the semiconductor processing chamber component itself, is placed on a tile 190 for testing. In some embodiments, where the testing is performed at a temperature of up to 50 degrees Celsius, the tile 190 may be interfaced with a heater 195. The heater 195 may be a resistive heater. The coupon 150 includes a coating layer 160 disposed over a base layer 155. The coating layer 160 may include defects 265, as shown in FIG. 2. During the test, the defects 265 in the coating layer 160 allow the base layer 155 to be exposed to a reagent 120. A reaction between the base layer 155 and the reagent 120 can be detected by the test station 100. In one embodiment, the base layer 155 may be aluminum, steel, metal alloy, or other material suitable for fabricating a semiconductor chamber component. The coating layer 160 is substantially non-reactive with the reagent 120. In one example, the coating layer 160 may be an aluminum oxide, fluorided aluminum oxide, anodized aluminum oxide, and yttrium oxide, among others. The coating layer 160 can be doped, for example by co-depositing cerium oxide, zirconium oxide, samarium oxide, other types of rare earth oxides and other elements and oxides thereof. Essentially, any coating layer can be tested as long as it is substantially non-reactive with the reagent.

In an embodiment of the disclosure, the test station 100 includes a hollow tube 110 with an open top end 112 and an open bottom end 114. The tube 110 may be composed of transparent polymer, quartz, glass material or other suitable material that does not react with the reagent. The tube 110 generally has a circular cross-section, though in some embodiments, the cross-section may have other shapes. In one example, the tube 110 is about 25 millimeters (mm) to about 50 mm in height, has an inner diameter of about 12.5 mm to about 38 mm, and an outer diameter of about 15 mm to about 45 mm. Thus, the wall of the tube 110 has a thickness of about 2.5 mm to about 6.5 mm. Also, the diameter of the tube 110 is substantially uniform along the length thereof. In another example, the thickness of the wall of the tube 110 is selected to provide sufficient strength and the diameter is selected to hold a sufficient quantity of reagent 120 while being sealingly urged against the coupon 150.

The bottom end 114 of the tube 110 is sealingly disposed against the coating layer 160. In one example, a seal 116 may be disposed along the circumference of the bottom end 114 in a manner that allows the seal 116 to prevent leakage of the reagent 120 between the tube 110 and the coupon 150. The seal 116 may be composed of an elastomer and substantially prevents the leakage of the contents of the tube 110 from migrating outside the tube 110. During testing of the coupon 150, the tube 110 contains the reagent 120, such as an acid or other suitable material that is capable of reacting with the base layer 155 but is substantially inert with the coating layer 160. In one example, the tube 110 holds about 20 milliliters (ml) to about 150 ml of the reagent 120. In some embodiments, the reagent 120 is a solution of less than 10% weight, such as about 5% by weight of hydrochloric acid, a solution of less than 10% weight, such as about 5% by weight of nitric acid or a solution of less than 10% weight, such as about 5% by weight of sulfuric acid. The reagent 120 is introduced into the tube 110 through the top end 112 or through the side of the tube 110 by an opening (not shown). In some embodiments, a pump 126 operates to deliver the reagent 120 from a reagent reservoir 128 to the tube 110 via a conduit 127. When the reagent 120 reacts with the base layer 155, a gaseous byproduct 225 is produced, as shown in FIG. 2. In some embodiments, the gaseous byproduct may take the form of bubbles.

A clamping mechanism 170 is utilized to urge the bottom end 114 of the tube 110 against the coating layer 160 during testing of the coupon 150. In some embodiments, the clamping mechanism 170 includes an actuator 172 connected to a beam 174. The beam 174 may be adjustable to accommodate different sizes of coupons 150 and tubes 110. The beam 174 is coupled to an arm 176 that applies downward pressure to the top end 112 of the tube 110 to sealingly hold the tube 110 against the coating layer 160. In one example, the beam 174 can be adjusted in a vertical direction to adjust the placement of the arm 176 with the height of the tube 110. The clamping mechanism 170 advantageously prevents the tube 110 from toppling over and spilling the reagent 120 during testing. The clamping mechanism 170 is normally used to directly clamp the coupon 150 under test to the tile 190 as shown in FIG. 1, or a table or other stable board in different embodiments.

A sensor 130 is attached to the top end 112 of the tube 110. In one embodiment, a sensor holder 140 retains the sensor 130 to the top end 112 of the tube 110. The sensor 130 is configured to detect the presence of the gaseous byproduct 225 of the reaction between the reagent 120 disposed in the hollow tube 110 and the base layer 155 disposed under the coating layer 160. Should the reagent 120 be slightly reactive with the coating layer 160, the sensor 130 is configured to selectively detect the presence of the gaseous byproduct 225 of the reaction between the reagent 120 and the base layer 155 relative to a gaseous byproduct of the reaction between the reagent 120 and the coating layer 160. In some embodiments, the gaseous byproduct of the reaction between the reagent 120 and the base layer 155 may be hydrogen gas, and accordingly, the sensor 130 is a hydrogen sensor.

In one example, the sensor 130 has a detection range of 100-1000 ppm of hydrogen gas. Change in the current or voltage output of the sensor 130 is indicative of a change in the amount of hydrogen gas being generated by exposure of the reagent 120 to the base layer 155. The sensor 130 can be calibrated using experimentally-determined values of these changes to correlate to the amount that the coating layer 160 has been compromised.

Lead-wires 131 may optionally be connected to the sensor 130 through a lead-wire storage device 134. In one embodiment, the sensor 130 is electrically powered by a power source 135 that provides 5V power supply between the sensor 130 and ground. A 4.75 k-Ohm resistor connects the sensor 130 to the power source 135.

The sensor holder 140, as shown in FIG. 1, is used to couple the sensor 130 to the open top end 112 of the tube 110 as mentioned above. The sensor holder 140 may attach to the sensor 130 using a self-locking mechanism (not shown) or any other suitable attachment technique. The sensor holder 140 protects the sensor 130 from corrosion by creating a barrier between the sensor 130 and the interior walls of the tube 110. The interior walls of the tube 110 are susceptible to condensation of the reagent 120 and water. The sensor holder 140 advantageously protects the circuitry within the sensor 130 that would otherwise come in contact with the walls of the tube 110 and may become corroded by the condensated reagent 120 disposed on the interior walls of the tube 110. The presence of the sensor holder 140, specifically the hollow cylindrical portion 346 (shown in FIG. 3) creates a barrier that prevents the sensor 130 from coming in contact with the walls of the tube 110, thus preventing the likelihood of corrosion caused by contact with the walls of the tube 110.

Figure 3:
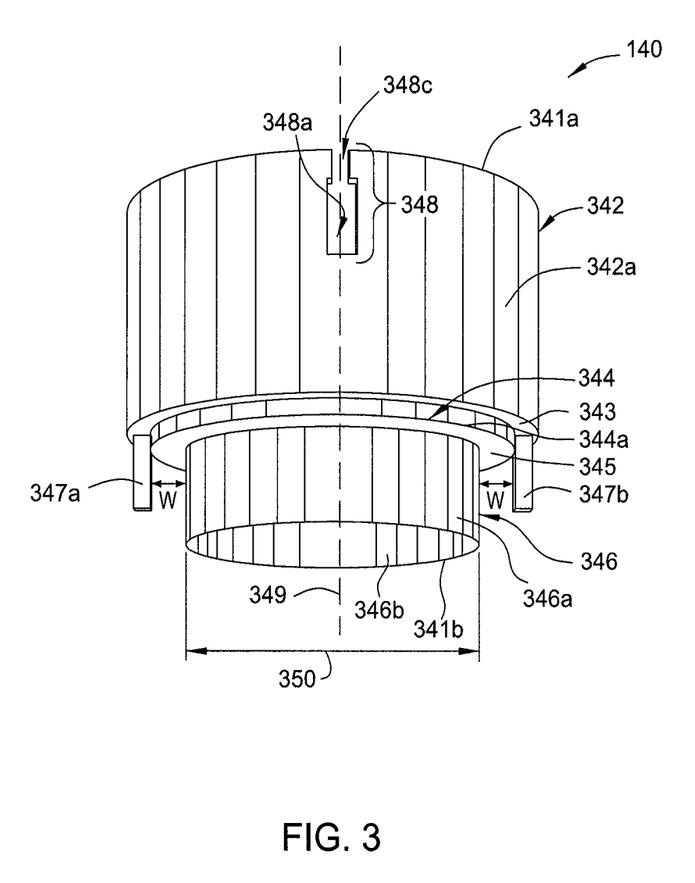
FIG. 3 is a perspective front view of a sensor holder configured to couple a sensor to the top end of the testing tube.
Figure 4:
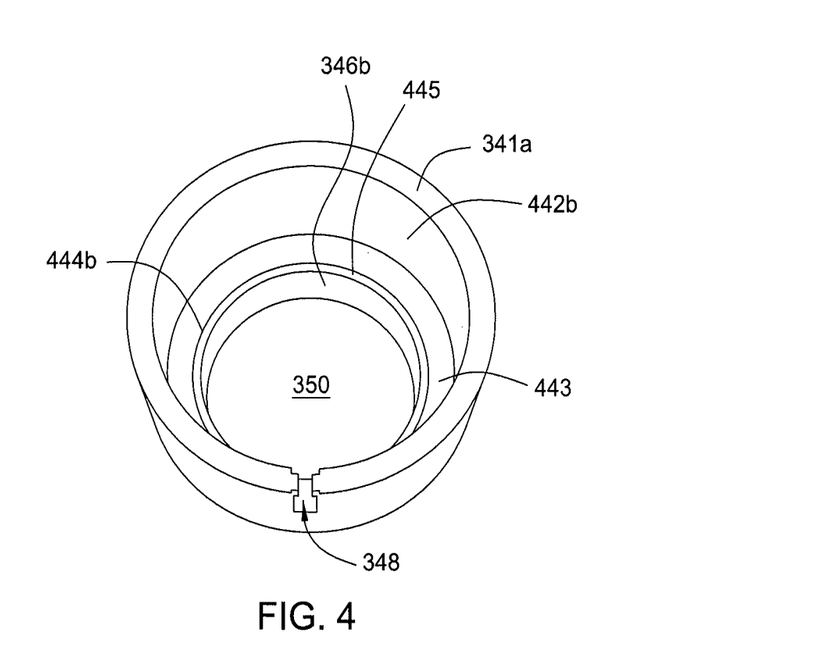
FIG. 4 is a perspective top view of a sensor holder configured to couple a sensor to the top end of the testing tube.
Figure 5:
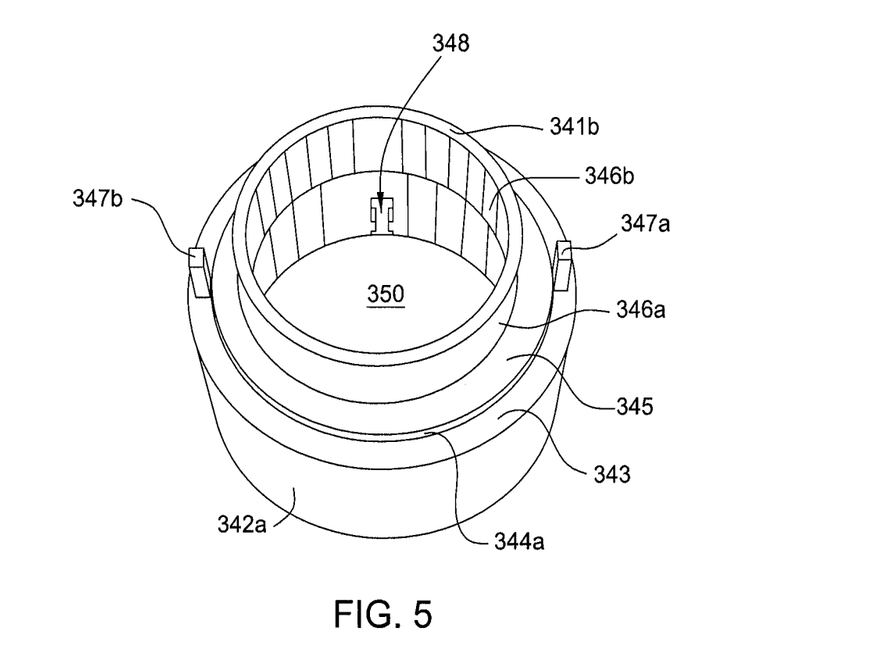
FIG. 5 is a perspective bottom view of a sensor holder configured to couple a sensor to the top end of the testing tube.

Referring now to FIG. 3, the sensor holder 140 includes three hollow cylindrical portions 342, 344 and 346. The first hollow cylindrical portion 342 has an outer wall 342a, an inner wall 442b, a ring-shaped top surface 341a and a ring-shaped bottom surface 343. A center axis 349 runs through the center of the ring-shaped top surface 341a and the ring-shaped bottom surface 343. The portion 342 is designed to allow the sensor 130 to contact the inner wall 442b and sit within. The diameter of the outer wall 342a around the axis 349 is selected commensurate with the diameter of the sensor 130 and the minimum thickness of the wall available for manufacturing the sensor holder 140. In some embodiments, the thickness is approximately 22.3 mm. The diameter of the inner wall 442b around the axis 349 is selected commensurate with the diameter of the sensor 130 and in some embodiments, is approximately 19 mm. The height of the portion 342 is selected commensurate with the height of the sensor 130 and in some embodiments, is approximately 19 mm. In the example of FIG. 3, the outer wall 342a has a facetted surface though in other embodiments, it may have a smooth surface. The portion 342 has a notch 348 having a wider gap 348a and a narrower gap 348c. The width of the wider gap 348a is selected commensurate with the thicknesses of the two lead-wires 131 coming out of the sensor 130. The width of the narrower gap 348c is selected commensurate with the thickness of one of the lead-wires 131 coming out of the sensor 130. In some embodiments, the wider gap 348a is approximately 1.4 mm wide and the narrower gap 348c is approximately 0.7 mm wide. Generally, the narrower gap 348c is selected to allow the lead-wires 131 to be removably retained in the wider gap 348a. The bottom surface 343 has two posts 347a and 347b protruding perpendicularly away from the surface 343. The posts 347a and 347b are placed at right angles on either side of the plane intersecting the notch 348 and the axis 349 and are designed to enable the sensor holder 140 to grip around the top end 112 of the tube 110. The posts 347a and 347b may have a cross section that is a square, a rectangle, annular, or any shape designed to fit around the top end 112 of the tube 110. The thickness of the posts 347a and 347b depend on the minimum thickness available for manufacturing and in some embodiments, is approximately 0.7 mm.

The second hollow cylindrical portion 344 projects from the bottom surface 343 and is concentric with the axis 349 and flushed against the posts 347a and 347b. The portion 344 has an outer wall 344a, an inner wall 444b, a ring-shaped top surface 443 and a ring-shaped bottom surface 345. In FIG. 3, the outer wall 344a has a facetted surface though in other embodiments, it may have a smooth surface. The third hollow cylindrical portion 346 projects from the bottom surface 345 of the portion 344 and is concentric with the axis 349. The portion 346 has a ring-shaped top surface 445, outer wall 346a, an inner wall 346b and a ring-shaped bottom surface 341b. The diameter of the portion 346 around the axis 349 is selected commensurate with the inner radius of the tube 110 and in some embodiments, is approximately 16 mm. A gap w between posts 347a and 347b and the outer wall 346a is designed to match the width of the thickness of the tube 110, which helps to attach the sensor holder 140 to the tube 110 in a detachable manner. The width of the gap w is selected commensurate with the thickness of the tube 110, and in some embodiments, is approximately 1.5 mm. In the example of FIG. 3, the outer wall 346a has a facetted surface though in other embodiments, it may have a smooth surface. The aperture 350 passes through the portions 342, 344 and 346 to create an opening through which the sensor 130 can contact the gaseous byproduct 225, as discussed in FIG. 2.

In some embodiments, the sensor holder 140 may be manufactured by three dimensional printing (or 3-D printing). In one embodiment, a computer (CAD) model of the sensor holder 140 is first made and then a slicing algorithm maps the information for every layer. A layer starts off with a thin distribution of powder spread over the surface of a powder bed. A chosen binder material then selectively joins particles where the object is to be formed. Then a piston which supports the powder bed and the part-in-progress is lowered in order for the next powder layer to be formed. After each layer, the same process is repeated followed by a final heat treatment to make the object. Since 3-D printing can exercise local control over the material composition, microstructure, and surface texture, various (and previously inaccessible) geometries may be achieved with this method.

In one embodiment, the sensor holder 140 as described herein may be represented in a data structure readable by a computer system with a computer-readable medium. The computer-readable medium may store the data structure that represents the sensor holder 140. The data structure may be a computer file, and may contain information about the structures, materials, textures, physical properties, or other characteristics of one or more articles. The data structure may also contain code, such as computer executable code or device control code that engages selected functionality of a computer rendering device or a computer display device. The computer readable medium may include a physical storage medium such as a magnetic memory, floppy disk, or any convenient physical storage medium. The physical storage medium may be readable by the computer system to render the article represented by the data structure on a computer screen or a physical rendering device, which may be an additive manufacturing device, such as a three-dimensional printer.

Referring to FIG. 1, the lead-wires 131 soldered to the designated output pins of the sensor 130 are coupled to a lead-wire storage device 134. The lead-wire storage device 134 connects the sensor 130 to the processing system 180 through connecting wire 185 and the power source 135 through the connecting wire 136. The lead-wire storage device 134 has a retractable end 132 which is configured to store an excess length of the lead-wires 131 of the sensor 130, thus reducing wire clutter and increasing wire flexibility. The lead-wire storage device may be a reel case having a retractable end 132 of length 1 meter, such as but not limited to, a reel case manufactured by StageNinja LLC.

A processing system 180 is connected to the sensor 130 via the connecting wire 185, as shown in FIG. 1. The processing system 180 is configured to determine exposure of the base layer 155 through the coating layer 160 in response to information about the presence of the gaseous byproduct 225 detected by the sensor 130. The processing system 180 includes a data acquisition module 182, an analog-to-digital converter 184 and a controller 186, which may be a computer.

Figure 6:
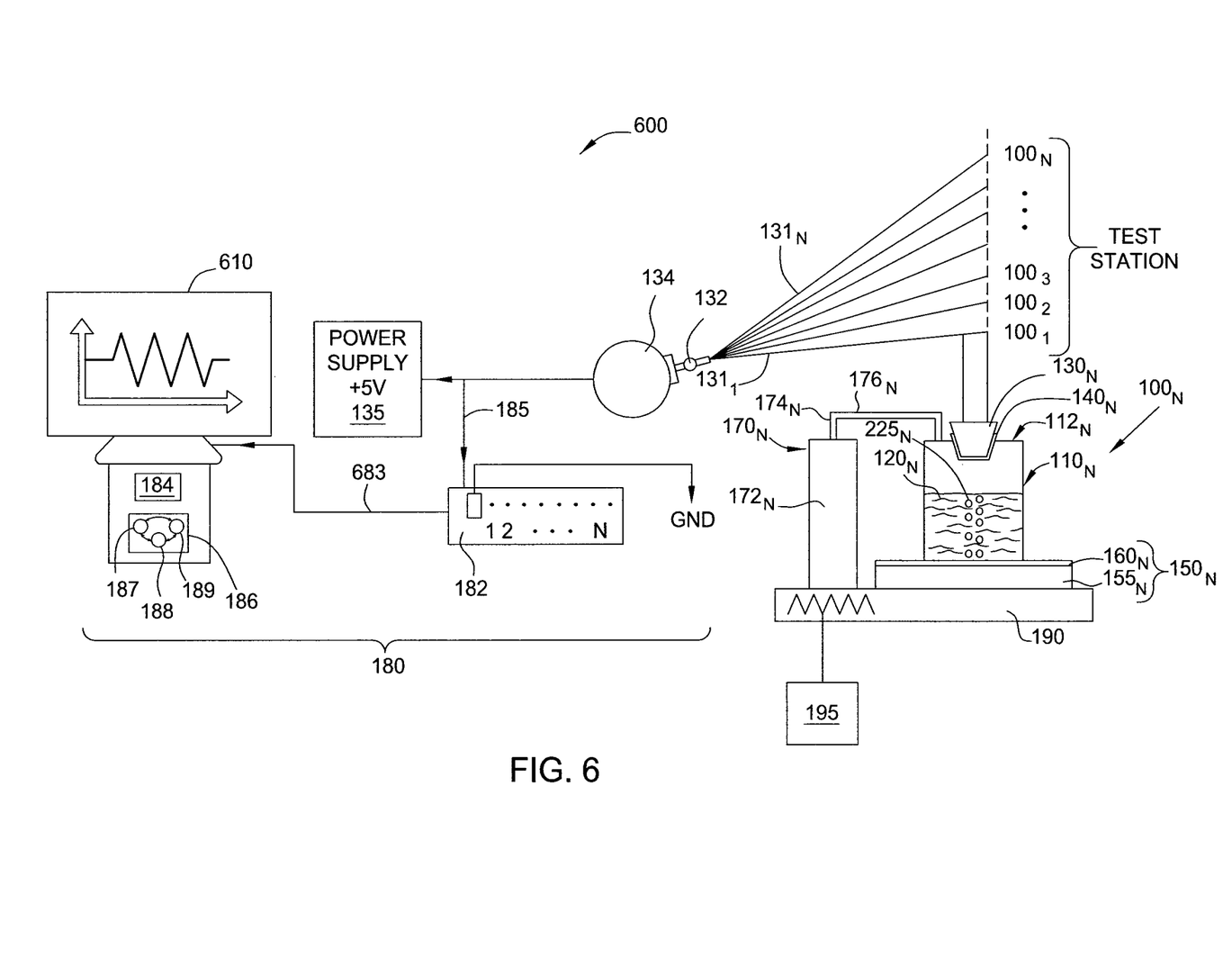
FIG. 6 is a schematic representation of a system for testing a coating over a semiconductor chamber component.

The data acquisition module 182 is connected to the sensor 130 by the connecting wire 185 coming out of the lead-wire storage device 134. The data acquisition module 182 is configured to acquire analog data from the sensor 130 corresponding to the presence or absence of gaseous byproduct 225. The analog data is then sent to the analog-to-digital converter 184 via the connecting wire 683, as shown in FIG. 6. In some embodiments, the connecting wire 683 is a universal serial bus (USB) cable. The analog-to-digital converter 184 converts the analog data into machine-readable digital form.

The controller 186 includes a central processing unit (CPU) 187, a memory 188, a display screen 610 (shown in FIG. 6), and a support circuit 189. The controller 186 is utilized to regulate the power applied to the sensor 130 from the power source 135 and monitor the voltage of the sensor 130. The CPU 187 may be any form of a general purpose computer processor used in an industrial setting. The memory 188 may be a random access memory, read only memory, floppy, or hard disk drive, or other form of digital storage. The support circuit 189 is conventionally coupled to the CPU 187 and may include cache, clock circuits, input/output systems, power supplies, and the like.

A fully-integrated and automated graphical system design software is used in creating test, measurement, and control applications for the test. When implemented within the controller 186, the software is used to create custom, event-driven user interfaces for measurement, control and analysis of the data measured from the sensor 130. In some embodiments, the software is used to create one or more graphical interfaces to allow visual inspection of the data from the sensor 130. The visual inspection is made from graphs where the voltage is plotted against time on the display screen. Failure times of the coating layer 160 down to the second are noted on the display screen automatically as the data is captured, for example by means of a light emitting diode (LED) turning red when a certain voltage increase is determined compared to calibrated values. At the same time, the software is configured to let the voltage-time graph run so that the increases in voltage are captured for subsequent analysis of the failure of the coating layer 160. In some embodiments, when the failure time for the coating layer 160 is not known, the software is configured to allow testing to be run for an infinite amount of time as long as the sensor 130 and the controller 186 are powered and no other part of the system fails. The software is used to export the data on voltage increases and failure times for subsequent analysis. In some embodiments, the software is configured to allow users to leave the test area while the tests are run and to receive alerts of events by text message or electronic mail, when they are away. In one example, the software used may be LabVIEW® Base Development System and Application Builder®. The software is licensed from National Instruments, installed and stored in the memory 188 of the controller 186. The Application Builder® software is used to create an application file to distribute the LabVIEW® Base Development System.

During the test, the reagent 120 is added into the tube 110 in the test station 100. Each test station 100 includes of the coupon 150, where the coating layer 160 is disposed over the base layer 155. As discussed above, the coupon may be a semiconductor chamber component, such as a liner, plasma screen, shield, cover ring, edge ring, chamber body, slit valve door or other chamber component. The reagent 120 is selected such that reagent 120 is substantially inert to the coating layer 160 but when exposed to the base layer 155 produces the gaseous byproduct 225. During the test, if the coating layer 160 is uniform and durable enough to survive exposure to the reagent 120 in the tube 110 for a certain amount of time, the coating layer 160 is deemed to be within manufacturing specifications. If the coating layer 160 has defects, the reagent 120 comes into contact with the base layer 155 beneath the coating layer 160 and produces the gaseous byproduct 225.

The presence of the gaseous byproduct 225 is detected by the sensor 130 attached to the top end 112 of the tube 110. The sensor 130 detects the presence of the gaseous byproduct 225 in the form of an increase in the voltage or current outputted by the sensor 130. The analog data about information on the presence or absence of the gaseous byproduct 225 is acquired by the data acquisition module 182, which transmits the analog data to the analog-to-digital converter 184 for conversion into machine-readable digital form. A controller 186 uses the digital information to determine the exposure of the base layer 155 through the coating layer 160. Software installed in the memory 188 of the controller 186 as described above in detail is used to save failure times down to the second and visually observe the voltage-time graphs corresponding to the digital information on a display screen 610 connected to the controller 186. The increase in voltages seen in the voltage-time graphs shows when and how the reagent 120 penetrates through the coating layer 160 to react with the base layer 155. Further analysis of the data gives a standardized quantitative measure of the failure of the coating layer 160.

In one aspect of the disclosure, a system 600 for testing a coating over a semiconductor chamber component is disclosed, as shown in FIG. 6. The system includes a processing system 180 and a plurality of test stations $100_1$, $100_2$, ... $100_N$, where N is a positive integer greater than 1. Each test station $100_N$ is placed on a tile 190, which may be connected to a heater 195. A plurality of coupons of semiconductor chamber component is placed on the tile 190. Each coupon $150_N$ includes a base layer $155_N$ and a coating layer $160_N$. Each test station $100_N$ includes a hollow tube $110_N$ having an open bottom end $114_N$ configured for sealingly engaging a coating layer $160_N$ of a semiconductor chamber component and a sensor $130_N$ attached to the top end $112_N$ by a sensor holder $140_N$. The sensor $130_N$ is configured to detect the presence of a gaseous byproduct $225_N$ of a reaction between a reagent $120_N$ disposed in the tube $110_N$ and the base layer $155_N$ of the coupon $150_N$ disposed under the coating layer $160_N$. The coating layer $160_N$ has defects $265_N$, which exposes the base layer $155_N$ such that the reagent $120_N$ reacts with the base layer $155_N$ to produce the gaseous byproduct $225_N$. Each test station $100_N$ is the same as the test station 100 as described above in detail and shown in FIGS. 1 and 2.

A clamping mechanism $170_N$ is utilized to urge the bottom end $114_N$ of the tube $110_N$ against the coating layer $160_N$. In some embodiments, the clamping mechanism $170_N$ includes an actuator $172_N$ connected to the beam $174_N$. The beam $174_N$ is coupled to an arm $176_N$ that applies downward pressure to the top end $112_N$ of the tube $110_N$ to hold the tube $110_N$ against the coating layer $160_N$. In one example, the adjustable beam $174_N$ can be adjusted in a vertical direction to adjust the placement of the arm $176_N$ with the height of the tube $110_N$.

A lead-wire $131_N$ from the sensor $130_N$ is coupled to a lead-wire storage device $134_N$. The lead-wire storage device 134 connects the sensor $130_N$ to the processing system 180 through the connecting wire 185 and the power source 135 through the connecting wire 136. The lead-wire storage device 134 has a retractable end $132_N$ which is configured to store an excess length of the lead-wires $131_N$, thus reducing wire clutter and increasing wire flexibility. The lead-wire storage device $134_N$ may be a case of reels, such as but not limited to the one manufactured by StageNinja LLC.

The processing system 180 is communicatively coupled to each sensor $130_N$ of the plurality of test stations $100_N$. The processing system 180 is configured to determine exposure of the base layer $155_N$ through the coating layer $160_N$ in response to information about the presence of the gaseous byproduct $225_N$ obtained by each sensor $130_N$. The processing system 180 is the same as the processing system 180 as described above in detail and shown in FIG. 1. The processing system 180 has a data acquisition module 182, an analog-to-digital converter 184 and a controller 186. In some embodiments, the controller 186 is a computer which includes a central processing unit (CPU) 187, a memory 188, a support circuit 189 and a display monitor 610, where plotted graphs of the data can be viewed.

Figure 7:
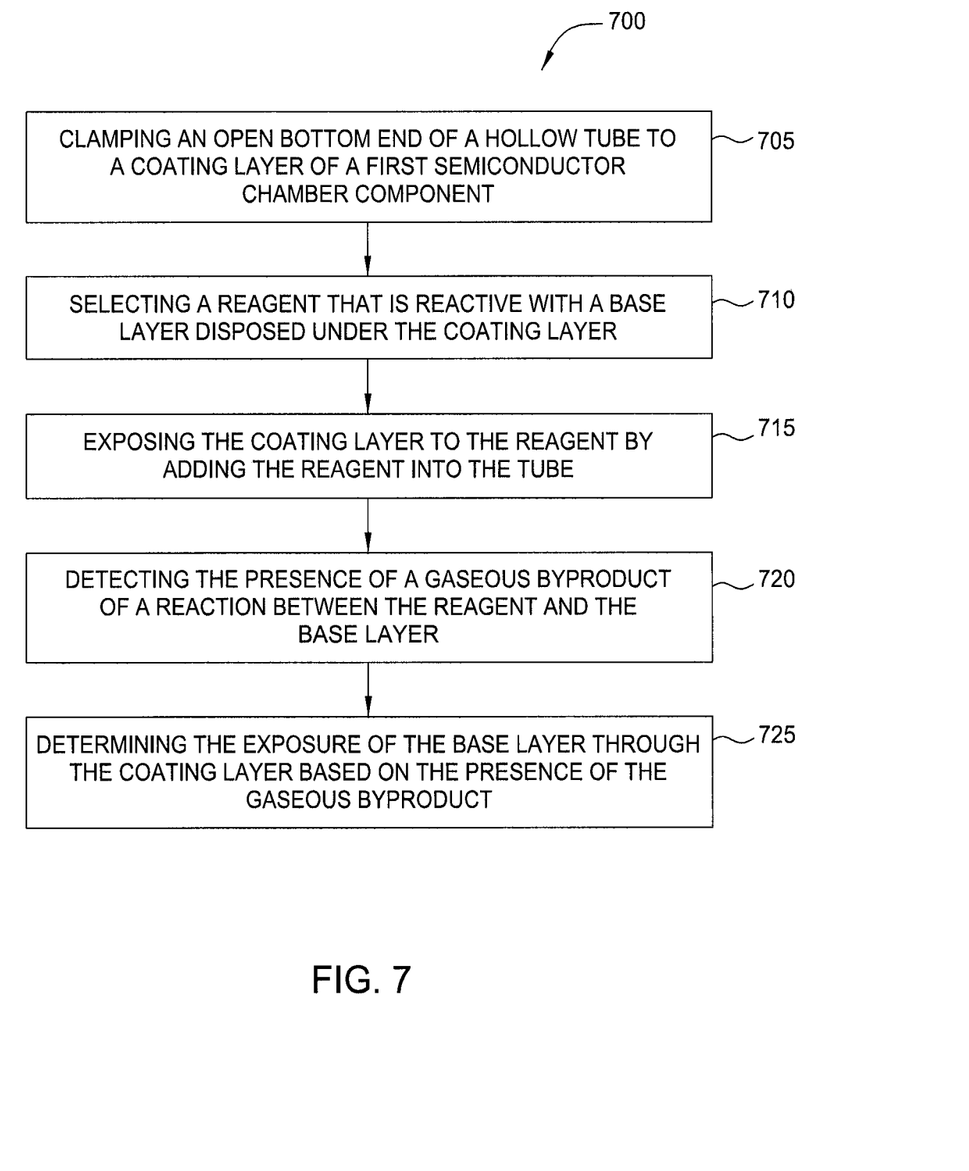
FIG. 7 is a block diagram of a method for testing a coating over a semiconductor chamber component.

In another aspect of the disclosure, a method 700 for testing a coating over a semiconductor chamber component is disclosed, as shown in the block diagram 700 in FIG. 7. As shown in the block 705, the method begins by clamping an open bottom end of a hollow tube to a coating layer of a first semiconductor chamber component. In block 710, a reagent is selected that is reactive with a base layer disposed under the coating layer and is inert to the coating layer.

In block 715, the coating layer of the first semiconductor chamber component is exposed to the reagent by adding the reagent into the tube. In one embodiment, the reagent is added to the tube utilizing a pump, for example, a reversible pump or syringe. Over time, if defects are present in the coating layer, the reagent reacts with the base layer disposed underneath the coating layer to release a gaseous byproduct.

In block 720, the presence of the gaseous byproduct is detected by a sensor attached to the top end of the hollow tube. The sensor detects the presence of the gaseous byproduct in the form of an increase in the voltage or current across simple circuitry connected to the sensor. The analog data about information on the presence or absence of the gaseous byproduct is acquired by a data acquisition module, which transmits the analog data to an analog-to-digital converter for conversion into machine-readable digital form.

In block 725, a controller uses the digital information on the presence or absence of the gaseous byproduct to determine exposure of the base layer through the coating layer. Software installed in the controller is used to save failure times down to the second and visually observe the voltage-time graphs corresponding to the digital information on a display screen connected to the controller.

The method 700 can be performed by a system comprising a plurality of test stations and a processing system, described in detail above. Each of the plurality of test stations can test the coating over a semiconductor chamber component at the same time as another. The processing system can acquire, process and analyze the data from each test station as well as control and automate the operation of the system through use of software.

In one embodiment, each test station includes a coupon, where the base layer is made of aluminum and the coating layer is made of an aluminum oxide, fluorided aluminum oxide, anodized aluminum oxide, and yttrium oxide. The reagent used is a solution containing 5% by weight of hydrochloric acid. During the test, if the coating layer is uniform and durable enough to survive exposure to the reagent in a tube for a certain amount of time, the coating layer is deemed to be free of defects, i.e., within manufacturing specifications. If the coating layer has defects, the reagent comes into contact with the aluminum beneath the coating layer and produces a stream of hydrogen gas according to the equation below:

$$6HCl(aq)+2Al(s)=2AlCl_3(aq)+3H_2(g)$$

The presence of hydrogen gas is detected by a sensor attached to the top end of the tube. The sensor detects the presence of the hydrogen gas in the form of change in the voltage outputted by the sensor. The analog data about information on the presence or absence of the hydrogen gas is acquired by a data acquisition module, which transmits the analog data to an analog-to-digital converter for conversion into machine-readable digital form. A computer uses the digital information to determine exposure of the aluminum layer through the coating layer. LabVIEW® software installed in the computer as described above in detail is used to save failure times down to the second and visually observe the voltage-time graphs corresponding to the digital information on a display monitor connected to the computer. The increase in voltages seen in the voltage-time graphs shows when and how the solution of 5% hydrochloric acid penetrates through the coating layer to react with the aluminum. Further analysis of the data gives a standardized quantitative measure of the failure of the coating layer.

In one example, an automated system having eight test stations on a single tile or multiple tiles is connected to a processing system to conduct simultaneous testing and quantitative failure analysis of up to eight test coupons. The data acquisition module correspondingly has eight data input channels that feed the data from each of the eight test stations to the software installed in the computer. LabVIEW® software is configured to read eight tests simultaneously. After the test is completed for each tube, the hydrochloric acid solution is removed from the tube, for example, by a reversible pump, pipette or other suitable device.

If the coating layer fails to survive the test, changes can be made during fabrication and treatment of the coating layers to optimize their performance and increase survival time.

While the foregoing is directed to particular embodiments of the present disclosure, it is to be understood that these embodiments are merely illustrative of the principles and applications of the present invention. It is therefore to be understood that numerous modifications may be made to the illustrative embodiments to arrive at other embodiments without departing from the spirit and scope of the present inventions, as defined by the appended claims.

What is claimed is:
1. A test station for testing a coating comprising:
a hollow tube having an open bottom end configured for sealingly engaging a coating layer of a semiconductor chamber component;

a sensor coupled to a top end of the hollow tube, the sensor configured to detect the presence of a gaseous byproduct of a reaction between a reagent disposed in the hollow tube and a base layer of the semiconductor chamber component disposed under the coating layer;

a sensor holder isolating and protecting the sensor coupled to the top end of the hollow tube from the reagent disposed in the hollow tube and configured to engage the sensor with the top end of the hollow tube; and a processing system communicatively coupled to the sensor, the processing system configured to determine exposure of the base layer through the coating in response to information about the presence of the gaseous byproduct obtained by the sensor.

2. The test station of claim 1 further comprising:
a clamping mechanism configured to urge the bottom end of the hollow tube against the coating layer.

3. The test station of claim 1 further comprising:
a seal disposed at the bottom end of the hollow tube and configured to seal the hollow tube with the coating layer.

4. The test station of claim 1 further comprising:
a power source configured to electrically power the sensor.

5. The test station of claim 1, wherein the processing system further comprises:
an analog to digital converter (ADC) coupled to the sensor and configured to convert an analog output signal generated by the sensor from analog to digital form.

6. A system for testing a coating comprising:
a plurality of test stations, each test station comprising:
a hollow tube having an open bottom end configured for sealingly engaging a coating layer of a semiconductor chamber component;
a sensor, the sensor coupled to a top end of the hollow tube, the sensor configured to detect the presence of a gaseous byproduct of a reaction between a reagent disposed in the hollow tube and a base layer of the semiconductor chamber component disposed under the coating layer; and
a sensor holder isolating and protecting the sensor coupled to the top end of the hollow tube from the reagent disposed in the hollow tube and configured to engage the sensor with the top end of the hollow tube; and
a processing system communicatively coupled to each sensor of the plurality of test stations, the processing system configured to determine exposure of the base layer through the coating in response to information about the presence of the gaseous byproduct obtained by each sensor.

7. The system of claim 6, wherein the processing system is communicatively coupled to each sensor of the plurality of test stations by at least one lead-wire.

8. The system of claim 7 further comprising:
a lead-wire storage device configured to store an excess length of the at least one lead-wire extending between the processing system and the sensor in each of the plurality of test stations.

9. The system of claim 6, wherein each test station further comprises:

a clamping mechanism configured to hold the bottom end of the hollow tube against the coating layer of the semiconductor chamber component disposed in the test station.

10. The system of claim 6, wherein each test station further comprises:
a seal disposed at the bottom end of the hollow tube and configured to seal the hollow tube against the coating layer of the semiconductor chamber component disposed in the test station.

11. The system of claim 6 further comprising:
a power source configured to electrically power the sensors in each of the plurality of test stations.

12. The system of claim 6, wherein the processing system further comprises:
at least one analog to digital converter (ADC) coupled to the sensor in each of the plurality of test stations.

13. The system of claim 1, wherein the sensor holder comprises:
a first hollow cylindrical portion configured retain the sensor, the first hollow cylindrical portion having a first bottom surface with a first post and a second post, the first post and second post protrude perpendicularly away from the first bottom surface and are configured to fit around the top end of the hollow tube;
a second hollow cylindrical portion projected from the first bottom surface, the second hollow cylindrical portion is flush against the first post and the second post; and
a third hollow cylindrical portion projected from a second bottom surface of the second hollow cylindrical portion, the third hollow cylindrical portion having an outer diameter substantially equal to an inner diameter of the top end of the hollow tube.

14. The system of claim 6, wherein the sensor holder comprises:
a first hollow cylindrical portion configured retain the sensor, the first hollow cylindrical portion having a first bottom surface with a first post and a second post, the first post and second post protrude perpendicularly away from the first bottom surface and are configured to fit around the top end of the hollow tube;
a second hollow cylindrical portion projected from the first bottom surface, the second hollow cylindrical portion is flush against the first post and the second post; and
a third hollow cylindrical portion projected from a second bottom surface of the second hollow cylindrical portion, the third hollow cylindrical portion having an outer diameter substantially equal to an inner diameter of the top end of the hollow tube.

15. The system of claim 1, wherein the sensor is configured to generate an analog output signal and the sensor is configured to detect the presence of the gaseous byproduct of the reaction between the reagent disposed in the hollow tube and the base layer of the semiconductor chamber component disposed under the coating layer through a change in the analog output signal of the sensor.

16. The system of claim 6, wherein the sensor is configured to generate an analog output signal and the sensor is configured to detect the presence of the gaseous byproduct of the reaction between the reagent disposed in the hollow tube and the base layer of the semiconductor chamber component disposed under the coating layer through a change in the analog output signal of the sensor.

* * * * *